United States Patent [19]

Chaiet et al.

[11] Patent Number: 5,008,187

[45] Date of Patent: Apr. 16, 1991

[54] ANTIFUNGAL FERMENTATION PRODUCT

[75] Inventors: Louis Chaiet; Sheldon B. Zimmerman, both of Springfield; Richard L. Monaghan, Somerset; George M. Garrity, Westfield, all of N.J.

[73] Assignee: Merck & Co., Inc., Rahway, N.J.

[21] Appl. No.: 278,385

[22] Filed: Dec. 1, 1988

[51] Int. Cl.$^5$ .................... C12P 19/00; C12P 17/00; A61K 31/70; C13K 13/00

[52] U.S. Cl. ............................. 435/72; 435/117; 435/929; 435/911; 536/1.1; 514/23

[58] Field of Search ............... 435/929, 117, 911, 72; 549/292; 424/122, 121; 536/1.1; 514/23

[56] References Cited

U.S. PATENT DOCUMENTS

| | | | |
|---|---|---|---|
| 3,932,621 | 1/1976 | Connor | 424/122 |
| 3,959,468 | 5/1976 | Burmeister | 424/122 |
| 4,191,825 | 3/1980 | Connor | 424/122 |
| 4,311,693 | 1/1982 | Hernandez | 424/122 |
| 4,828,992 | 5/1989 | De Val et al. | 435/929 |

OTHER PUBLICATIONS

The Merck Index, 9th Ed., 1983, pp. 248, 276, 669 and 773.

Westley et al., *J. of Antibiotics*, vol. 27, 1974, pp. 288–297.

*Primary Examiner*—Douglas W. Robinson
*Assistant Examiner*—Irene Marx
*Attorney, Agent, or Firm*—Alice O. Robertson; Charles M. Caruso

[57] ABSTRACT

A new antifungal agent which exhibits a moderately broad spectrum of activity towards filamentous fungi and also against Cryptococcus species of the yeast fungi, and which has been isolated from a solid stationary fermentation of an unidentified species of Fusarium is described.

6 Claims, 3 Drawing Sheets

ANTIFUNGAL FERMENTATION PRODUCT

BACKGROUND OF THE INVENTION

The present invention is concerned with a compound produced by cultivation of a microorganism of the Fusarium species and also with the use of the compound for the control of fungi, particularly filamentous fungi and also Cryptococcus species.

DETAILED DESCRIPTION OF THE INVENTION

Figure 1:
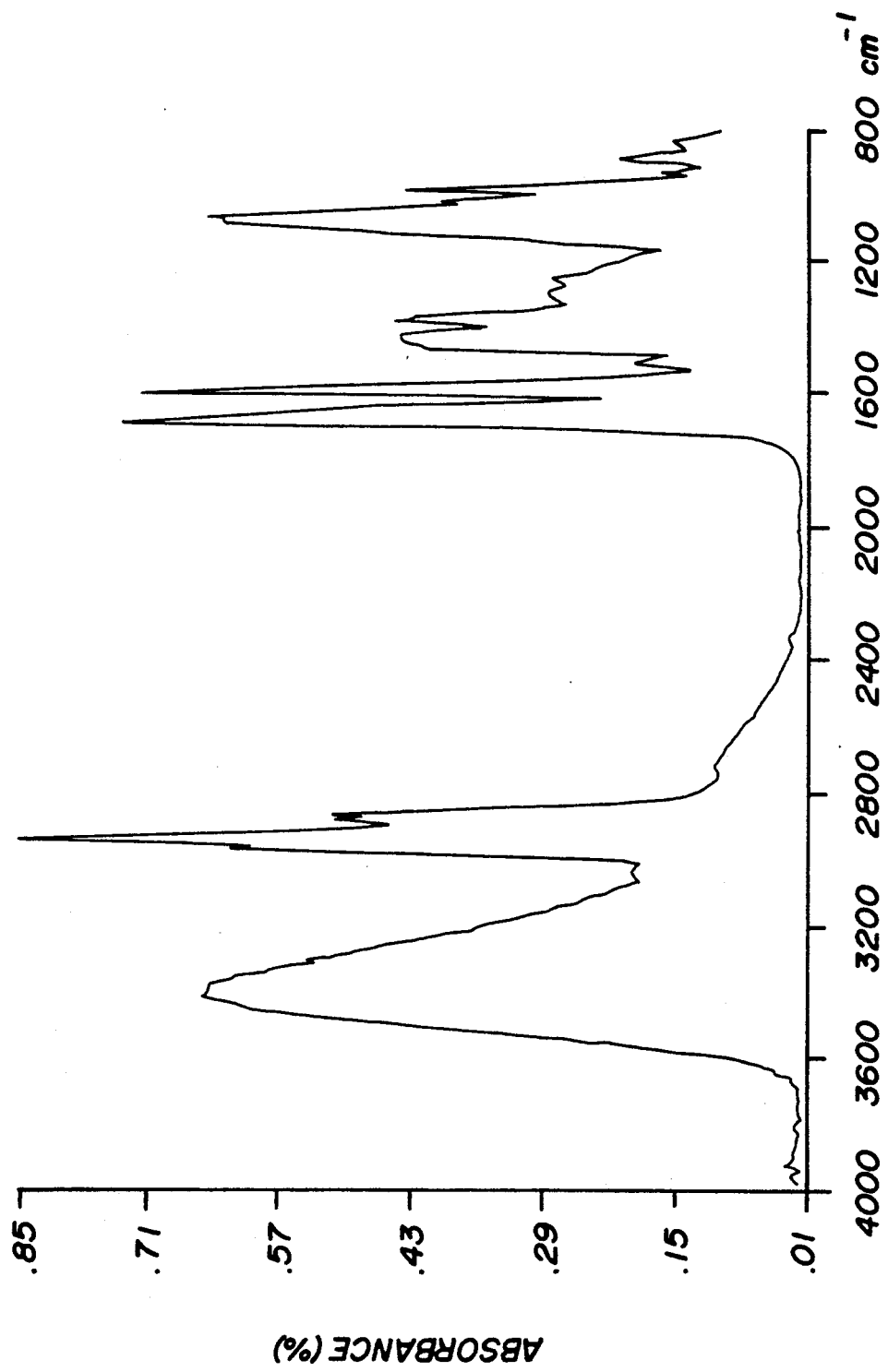
Figure 2:
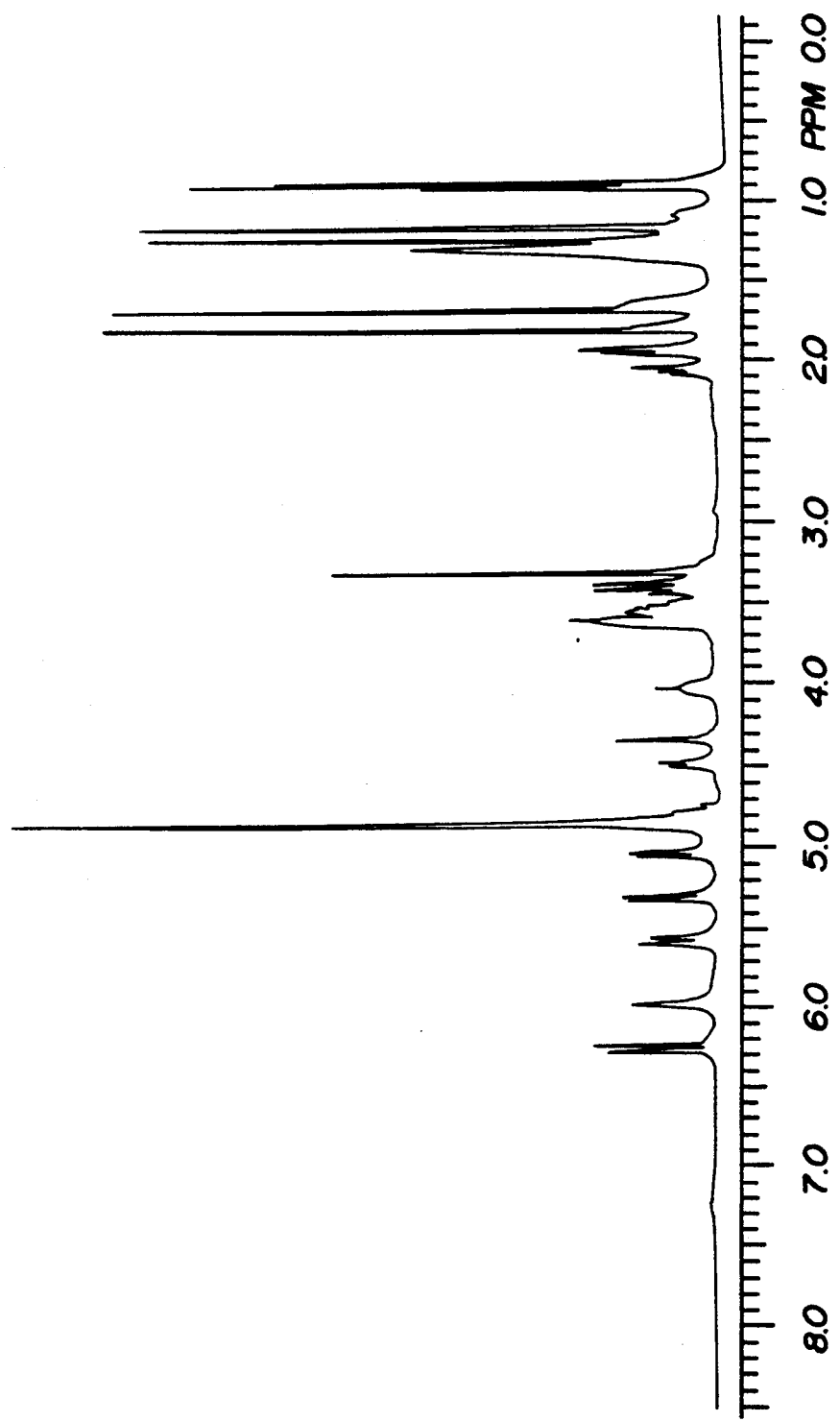
Figure 3:
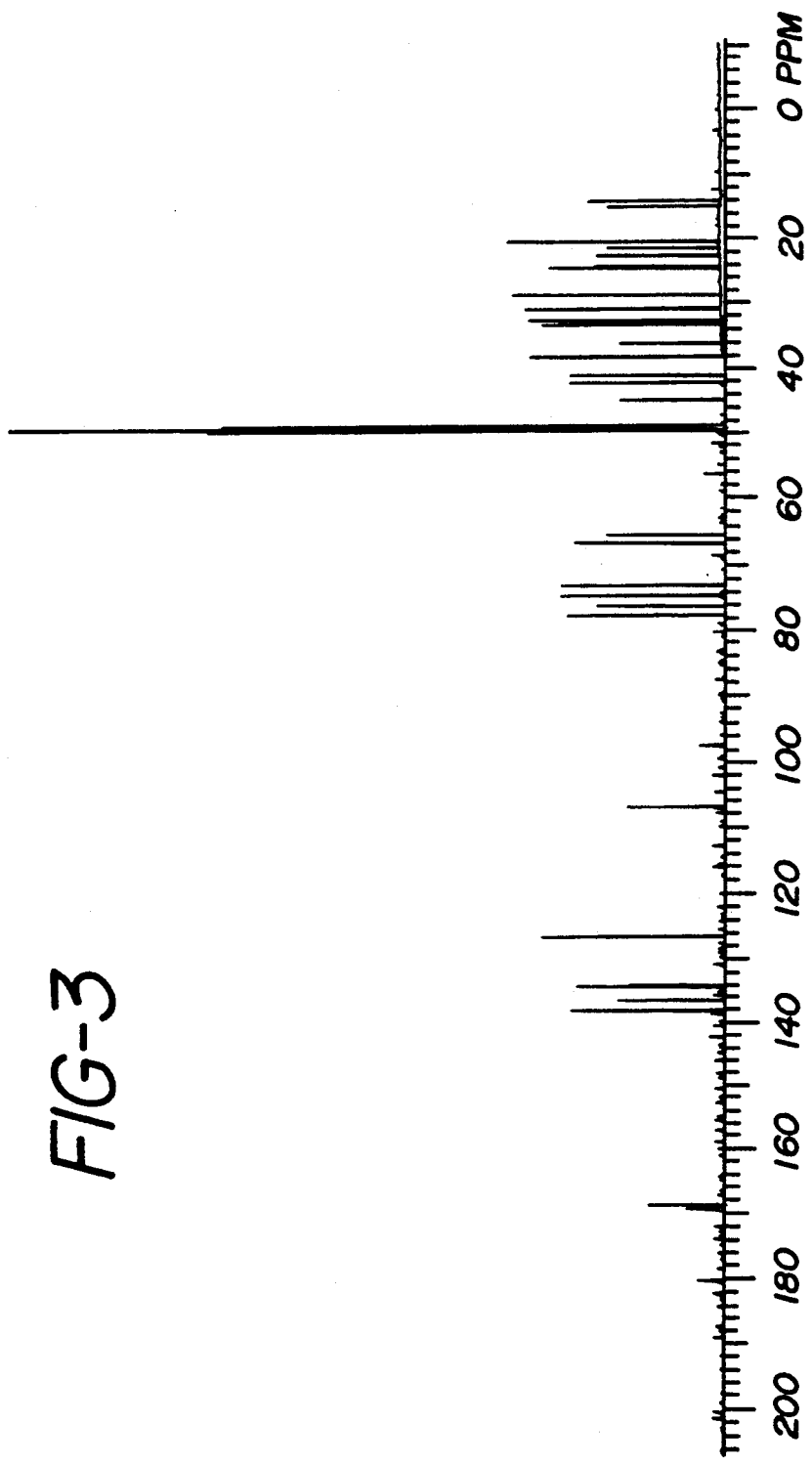

The novel agent, which may hereinafter be designated Compound I, is a white solid characterized by the following physico-chemical properties:
(1) Molecular weight: 606 (FAB-MS)
(2) Molecular formula: $C_{34}H_{54}O_9$ by EI-HRMS (calcd. for $C_{34}H_{54}O_9+Si_6C_{17}H_{51}$ [M++TMS6−CH3] 1023.5905; found 1023.5860)
(3) IR spectral data: The IR spectrum (KBr) is as seen in FIG. 1.
(4) $^1H$ NMR spectral data: The $^1H$ NMR spectrum recorded in $CD_3OD$ at ambient temperature and referenced to tetramethylsilane (TMS) at zero ppm using the solvent peak at δ 3.30 as internal reference is as seen in FIG. 2.
(5) $^{13}C$ NMR spectral data: The $^{13}C$ NMR spectrum recorded in $CD_3OD$ at ambient temperature gave the following chemical shifts in ppm downfield of tetramethyl silane (TMS) using the solvent peak at 49.0 ppm as internal reference: 13.5, 14.5, 20.2, 21.2, 22.4, 23.7, 24.1, 28.4, 30.7, 32.3, 33.1, 36.2, 38.1, 41.2, 42.1, 44.9, 65.7, 66.9, 73.3, 74.7, 76.4, 77.6, 78.0, 97.9, 107.3, 126.8, 127.0, 134.4, 134.7, 137.0, 138.5, 169.2, 169.7 and 181.0. The spectrum is also seen in FIG. 3.
(6) UV spectral data: MeOH/max nm (E 1%/1 cm) 206(897), 238(897), 282(273)
(7) TLC: Silica gel 60 (E. Merck) 70:30 $CH_2Cl_2:CH_3OH$, $R_f$ 0.46

The compound is soluble From the foregoing spectral data the compound is believed to have the following formula

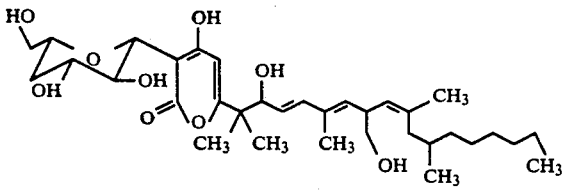

in a variety of organic solvents such as methanol, ethanol, dimethylformamide, dimethyl sulfoxide, ethyl acetate and the like.

The compound has been found to be active against a moderately broad spectrum of filamentous fungi and yeast organisms, rendering it adaptable for therapeutic applications when pathogens are of concern but adaptable also for industrial and agricultural applications.

The antifungal agent of the present invention, Compound I, having the characteristic above-described properties may be produced by fermentation of a previously unknown strain of the microorganism belonging to the genus Fusarium designated MF 5000 in the culture collection of Merck & Co., Rahway, N.J. and recovering said compound from the culture broth. A sample of the culture capable of producing the compound has been deposited under the Budapest Treaty in the culture collection of the American Type Culture Collection, 12301 Parklawn Drive, Rockville, Md. 20852. The sample has been assigned the accession number ATCC No. 20883.

The morphological and cultural characteristics are as follows:

MORPHOLOGICAL CHARACTERISTICS

Microconidia are generally unicellular, oval to ellipsoidal, borne singly in short conidiophores and held in a gelatinous mass, 1.8–2.4 microns×3.6–4.8 microns.

Macroconidia are generally 4–5 celled with dorsal and ventral surfaces parallel for most of their length, 3.6–4.8 microns×48–60 microns. The apical cell is rounded and the basal cell shows a rounded foot-shape.

Chlamydospores are smooth-walled, terminal and intercalary, globose, usually formed singly.

CULTURAL CHARACTERISTICS

On Czapek-Dox agar and potato dextrose agar colony is rapid growing, flocculose becoming felted, pale pinkish tan with no distinctive reverse color.

On cornmeal agar colony is slower-growing, felted, white with no distinctive reverse color.

On Sabouraud maltose agar and yeast extract malt extract agar colony is rapid-growing, flocculose becoming more felted, cream to pale tan in color with no distinctive reverse color.

A careful comparison of the foregoing data with published descriptions in "Fusarium Species" by Paul E. Nelson et al., Penn State Univ. Press, U.S.A., 1983 and in "The Genus Fusarium" by C. Booth, Commonwealth Mycological Institute, Kew Surrey, England, 1971, indicates that the organism can be identified as belonging to the genus Fusarium; it is however as yet of an unidentified species.

Since it is known in the art that the properties of microorganisms may be varied naturally and artificially, all strains of the genus Fusarium including varieties and mutants, whether obtained by natural selection, produced by action of mutating agents such as ionizing radiation or ultraviolet irradiation or by action of chemical mutagens such as nitrosoguanidine, may be employed for producing the compound of the present invention.

The compound of the present invention may be produced by the aerobic fermentation of a suitable solid nutrient medium under conditions as hereinafter described with a producing strain of Fusarium sp. MF 5000.

Suitable nutrient media contain sources of carbon and nitrogen assimilable by the microorganism and generally low levels of inorganic salts. In addition, the fermentation media may contain traces of metal necessary for the growth of the microorganisms and production of the desired compound. These are usually present in sufficient concentrations in the complex sources of carbon and nitrogen, which may be used as nutrient sources, but can, of course, be added separately to the medium, if desired.

Although carbon may be supplied with appropriate amounts and/or combinations of dextrose sucrose, maltose, glycerol, lactose, dextran, cerelose and the like, and nitrogen may be supplied with yeast extracts, yeast hydrolysates, yeast autolysates, casein hydrolysates, corn steep liquors, distillers solubles and the like, it is preferred that a complex source be employed in a solid medium. Most preferred is a solid medium using millet as a source of carbon and nitrogen.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, copper, cadmium and the like. These are usually present in sufficient concentrations in the complex sources of carbon and nitrogen, which are preferably used as nutrient sources, but can, of course, be added separately to the medium, if desired.

The media most suitable for growing strains of Fusarium sp. MF 5000 are those based on millet. The media described below are merely illustrative of the media which may be employed and are not intended to be limiting.

| Media | Weight or Volume Per 250 ml Flask |
|---|---|
| Medium A | |
| Millet | 15.0 g |
| Yeast extract | 0.1 g |
| Alfalfa meal | 0.1 g |
| Water | 25 ml |
| Medium B | |
| Millet | 15 g |
| Yeast extract | 0.5 g |
| Sodium tartrate | 0.1 g |
| Ferric sulfate.7H$_2$O | 0.01 g |
| Sucrose | 0.5 g |
| Alfalfa | 0.5 g |
| Water | 15 ml |
| Medium C | |
| Millet | 15 g |
| Yeast extract | 0.5 g |
| Sodium tartrate | 0.1 g |
| Ferric sulfate.7H$_2$O | 0.01 g |
| Silica gel | 0.5 g |
| Alfalfa | 0.5 g |
| Monosodium glutamate | 0.1 g |
| Corn oil | 0.1 ml |
| Water | 15 ml |
| Medium D | |
| Millet | 15 g |
| Yeast extract | 0.5 g |
| Sodium tartrate | 0.1 g |
| Ferric sulfate.7H$_2$O | 0.01 g |
| Water | 15 ml |
| Medium E | |
| Millet Base | 15 g |
| Yeast extract | 0.5 g |
| Sodium tartrate | 0.1 g |
| Ferric sulfate.7H$_2$O | 0.01 g |
| Monosodium Glutamatic Acid | 0.1 g |
| Corn oil | 0.1 ml |
| Water | 15 ml |

For producing the compounds of the present invention, a fermentation broth containing Fusarium sp. MF 5000 is prepared by inoculating mycelia of the antibiotic-producing organism into a suitable medium and then cultivating under aerobic conditions.

The procedure generally is first to inoculate a preserved source of culture from an agar slant containing nutrient medium into a nutrient seed producing medium and to obtain, preferably through a two step procedure, growth of the organisms which serve as seeds in the production of the antifungal agent.

In this process, a slant section of a preserved culture of MF 5000 is inoculated in an appropriate liquid nutrient seed medium and the flasks incubated with or without agitation at temperatures in the range of from about 25° C. to about 30° C., usually about 28° C. Agitation when employed, may be up to about 400 RPM, preferably, about 200 to 220 RPM. The incubation is carried out over a period of from 1 to 10 days. When growth is abundant, usually between 2 and 4 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 2 days.

The growth is then employed to inoculate the production medium. The fermentation production medium inoculated with the culture growth is incubated for 3 to 30 days, preferably 7 to 21 days. The fermentation may be conducted at temperatures ranging from about 20° to 40° C. For optimum results, temperatures in the range of from about 24° to 26° C. are preferred. After the appropriate period for production of the desired compound, the latter is recovered from the fermentation medium.

The active material may be recovered by:

(1) adding aqueous acetone to release the product from the solid materials in the medium (2) concentrating the aqueous acetone solution to a small volume of aqueous solution (3) bringing the aqueous solution into contact with a non-ionic absorbent and subjecting the material to at least one chromatographic separation wherein in the chromatographic separation or separations, the eluates exhibiting activity against Penicillium species are combined and then concentrated to recover Compound I.

The exact steps may vary somewhat depending the solvent employed and the adsorbent or combination of adsorbents employed.

In carrying out the first step, aqueous acetone solvent is added to the fermentation medium and thoroughly mixed. The mixture is then filtered, the aqueous acetone filtrate concentrated to remove the acetone and to obtain an aqueous solution. The solution is applied to a column of non-ionic resins such as sytrene - divinylbenzene resins available commercially as Diaion HP 20, HP-30 or HP-40 (Mitsubishi Chemical Industries, Ltd). Other adsorbent such as silica gel or dextran adsorbent available under the trade name Sephadex LH-20 (Pharmacia) also may be employed.

The product may be recovered from the column by eluting with alcohol, preferably methanol. The fractions exhibiting activity against Penicillium species are combined and the solvent vaporized to recover the crude product in an aqueous concentrate. The pH is adjusted to 5.7 and the concentrate then extracted with a water immiscible solvent such as ethyl acetate. The extract is dried and the solvent evaporated off to obtain the crude product as residue. The residue product may be purified by chromatography. The purification is carried out first on a silica gel column and developing the column with a methanol gradient in methylene chloride, and then after combining the fractions most active against Penicillium, employing LiChroprep RP-18 column and developing with aqueous methanol to recover Compound I in the eluate.

The compound has excellent antifungal properties against many filamentous and many yeast organisms rendering it useful for the control of fungi in therapeutic and non-therapeutic applications. It also has antibacterial properties. Minimum inhibiting concentration against representative fungal organisms may be seen in the results of tests carried out by the agar dilution method in which an aqueous suspension of the metabolite was solubilized by adding a small amount of methanol. Further dilutions were made employing water. The diluted samples were added to molten agar to produce final concentrations of 512 μg/ml and lower. The molten agar was yeast nitrogen base agar prepared by adding 1 part of sterile yeast nitrogen base agar to 9 parts 2% Difco agar. The results are seen in the following table:

| Organism | Strain | MIC (μg/ml) |
|---|---|---|
| Aspergillus niger | MF442 | 3.1 |
| Aspergillus niger | MF11 | 1.6 |
| Cephalosporium sp. | MF4641 | 12.5 |
| Ceratocystis ulmi | MF4042 | 25.0 |
| Cercospora beticola | MF4608 | 4.0 |
| Fusarium oxysporium | MF4014 | 25.0 |
| Penicillium sp. | MF5014 | 3.1 |
| Penicillium sp. | MF5020 | 1.6 |
| Phoma sp. | MF4332 | 3.1 |
| Scopulariopsi communis | MF3769 | 6.2 |
| Trichoderma lignorum | MF3560 | 6.2 |
| Trichoderma sp. | MF4064 | 1.6 |
| Ustilago maydis | MF1996 | 8.0 |
| Verticillium serrae | MF3794 | 25.0 |
| Aspergillus fumigatus | MF4839 | 64.0 |
| A. flavus | MF383 | 64.0 |
| Candida pseudotropicalis | MY1100 | 25.0 |
| C. rugosa | MY1022 | 25.0 |
| C. tropicalis | MY1012 | 25.0 |
| Cryptococcus neoformans | MY1046 | 8.0 |
| Cr. neoformans | MY1050 | 32.0 |
| Cr. neoformans | MY1051 | 128.0 |
| Cr. albidus | MY1070 | 8.0 |
| Cr. laurentii | MY1074 | 8.0 |
| Cr. laurentii | MY1073 | 6.2 |
| Cr. laurentii | MY1077 | 12.5 |
| Debaryomyces guilliermondi | MY321 | 6.2 |

In view of the broad spectrum of activity, the product of the present invention is adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi on inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of Compound I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture may be employed in compositions in an inert carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof. These compositions may be employed by applying to the surface of or incorporating in the medium to be protected in antifungally effective amount of Compound I.

The following examples illustrate the invention but are not to be construed as limiting:

EXAMPLE I

Fermentation

A culture identified initially as MM3 and subsequently designated MF 5000 was inoculated into 54 milliliters of KF seed medium of the composition given below in an unbaffled 250 milliliter Erlenmeyer flask and the inoculated medium incubated for 4 days at 25° C. with agitation to permit growth to occur.

KF Medium

| Corn steep liquor | 5 grams |
|---|---|
| Tomato paste | 40 grams |
| Oat flour | 10 grams |
| Cerelose | 10 grams |
| Trace elements mix | 10 milliliters |
| Distilled water | to 1000 milliliters |
| presterile pH 6.8 | |
| Trace elements: | |
| $FeSO_4.7H_2O$ | 1 gram |
| $MnSO_4.4H_2O$ | 1 gram |
| $CuCl_2.2H_2O$ | 25 milligrams |
| $CaCl_2$ | 100 milligrams |
| $H_3BO_3$ | 56 milligrams |
| $(NH_4)_6MoO_4.4H_2O$ | 19 milligrams |
| $ZnSO_4.7H_2O$ | 200 milligrams |
| Distilled water | to 1000 milliliters |

EXAMPLE I (cont'd)

At the end of this growing period, a 2 milliliter portion of the seed medium was used to inoculate a 250 milliliter unbaffled Erlenmeyer flask containing MMY8 production medium prepared in the following manner:

15 grams of millet, 0.1 gram of yeast extract, 0.1 gram alfalfa meal, and 15 milliliters of distilled water were combined in a 250 milliliter Erlenmeyer flask and autoclaved; thereafter 10 milliliters of distilled water was added and the flask reautoclaved.

The inoculated production medium was incubated at 25° C. for 9 days with agitation at 220 rpm. At harvest, acetone was added to the flask to a final volumetric concentration of 40 percent. Portions of the various solvent growth medium mix was employed in biological assays.

EXAMPLE II

PRODUCTION OF COMPOUND I

Fermentation

Five separate fermentations were carried out for the production and isolation of Compound I.

For all fermentations culture MM3 was inoculated into 54 milliliters of KF seed medium in unbaffled Erlenmeyer flasks. The seed medium was incubated for two days at 28° to 30° C. with agitation of 220 rpm whereupon growth took place therein. After growth, 2 milliliter portions of seed media were used to inoculate production media MMY8, MMY2 and MMY9. The production media after inoculation were incubated for 19 days at 25° C. with agitation at 220 rpm to produce the desired antibiotic compound and thereafter harvested.

At harvest, acetone was added to each of the flasks to a final volumetric concentration of 40 percent of the medium. The solvent growth medium slurries thus obtained were combined and employed in the isolation hereinafter described.

The production media above employed were of the following contents and were prepared for use in the manner summarized below.

Medium MMY2 contained per 250 milliliter Erlenmeyer flask: 15.0 grams wheat, 0.1 gram yeast extract, 0.1 gram alfalfa meal, 5.0 milliliters of trace elements mix, and 25.0 milliliters of distilled water.

Medium MMY8 contained per 250 milliliter Erlenmeyer flask: 15.0 grams millet, 0.1 gram yeast extract, 0.1 gram alfalfa meal, 5.0 milliliters of trace elements mix, and 25.0 milliliters of distilled water.

Medium MMY9 contained per 250 milliliter Erlenmeyer flask: 15.0 grams millet, 5.0 milliliters of trace elements, 0.2 gram sodium tartrate, 0.2 gram potassium chloride, 0.2 gram magnesium sulfate heptahydrate, 0.5 gram sodium nitrate, 0.5 gram monobasic acid potassium phosphate, 10.0 milliliters of distilled water.

In the preparation of the media, the flask and contents were autoclaved, then an additional 10.0 milliliters of distilled water was added and the flasks and contents reautoclaved.

The media were then employed in the isolation.

Isolation

The contents of thirty five 250 milliliter Erlenmeyer flasks, each containing 40 milliliters of solid phase fermentation medium, were extracted with 50 percent aqueous acetone at room temperature for 25 hours to obtain 1200 milliliters of extract. (Forty percent of the combined media originated from growth in MMY8; forty percent from growth in MMY9 and 20 percent from growth in MMY2.) The fermentation media were obtained by incubating at 25° C. for 9 days under stationary conditions, the production medium described in Example I. The extract was evaporated into 400 milliliters of water and adsorbed on a 120 milliliter column of Diaion HP-20 resin. The resin was washed with 120 milliliters of water and the active material eluted with 350 milliliters of methanol. Agar diffusion plates containing an unidentified Penicillium species were used to monitor the eluates for active fractions. The solvent was evaporated from the eluate to the obtain 2.1 grams of solids which were placed in 100 milliliters of water and the resulting solution adjusted to pH 5.7. The aqueous solution was extracted with three equal portions of ethyl acetate. The ethyl acetate extracts were dried with magnesium sulfate and the dried extracts evaporated to obtain 1.1 grams of drug powder as residue.

The powder having antifungal activity was dissolved in 9.5 milliliters of methylene chloride and chromatographed on a 30 gram column of silica gel 60 (E. Merck). A methanol gradient in methylene chloride was used to develop the chromatogram. The activity was eluted in fractions containing 10–20 percent methanol. The most active fractions were combined and evaporated to dryness to obtain crude solid product in a yield of 554 milligrams.

The solid product was purified by dissolving it in 2.4 milliliters of 3:1 methanol/water and chromatographing the mixture on a 180 milliliter Lichroprep RP-18 reverse phase (E. Merck) column equilibrated with 75 percent aqueous methanol and collecting 4 milliliter fractions.

The most active fractions were combined, evaporated to dryness and the residue dissolved in 4 milliliters of ethyl acetate. Hexane was added whereupon Compound I was obtained as fine crystals in a yield 102 milligrams. The product is an acidic molecule with a molecular formula of $C_{34}H_{54}O_9$ and having physicochemical properties previously summarized.

What is claimed is:

1. An antifungal antibiotic compound having the formula

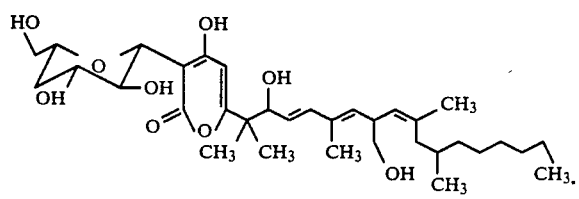

2. An antifungal antibiotic compound which is a white solid having the following physico-chemical properties:

(1) Molecular weight: 606 (FAB-MS)

(2) Molecular formula: $C_{34}H_{54}O_9$ by EI-HRMS (Calcd. for $C_{34}H_{54}O_9 + Si_6C_{17}H_{51}$ $[M^+ + TMS_6 - CH_3]$ 1023.5905; found 1023.5860)

(3) IR (KBr) as seen in FIG. 1.

(4) $^1H$ NMR in $CD_3OD$ as seen in FIG. 2

(5) $^{13}C$ NMR chemical shifts in $CD_3OD$ at 400 MHz of: 13.5, 14.5, 20.2, 21.2, 22.4, 23.7, 24.1, 28.4, 30.7, 32.3, 33.1, 36.2, 38.1, 41.2, 42.1, 44.9, 65.7, 66.9, 73.3, 74.7, 76.4, 77.6, 78.0, 97.9, 107.3, 126.8, 127.0, 134.4, 134.7, 137.0, 138.5, 169.2, 169.7, 181.0 ppm.

(6) UV: $\lambda MeOH/max$ nm (E 1%/1 cm) 206(897), 238(897), 282(273)

(7) TLC: Silica gel 60 70:30 $CH_2Cl_2:CH_3OH$ Rf 0.46; and which is produced by the cultivation of strain Fusarium ATCC No. 20883.

3. An antifungal composition which comprises a compound of claim 2 in admixture with a biologically inert carrier with the aid of a surface active dispersing agent.

4. A composition according to claim 3 in which the carrier is a pharmaceutically acceptable carrier.

5. A method for inhibiting fungal growth which comprises applying to the site where growth is to be controlled, an antifungally effective amount of the compound of claim 2.

6. A process for producing the antibiotic compound of claim 2 comprising aerobically cultivating a culture of Fusarium ATCC No. 20883 in a medium comprising millet as a source of carbon and nitrogen and isolating the compound.

* * * * *